United States Patent [19]

Malin et al.

[11] Patent Number: 4,468,462

[45] Date of Patent: Aug. 28, 1984

[54] VECTORS FOR CLONING IN STREPTOMYCES

[75] Inventors: Nancy E. Malin, Cupertino, Calif.; Jeffrey T. Fayerman, Indianapolis, Ind.; Michael D. Jones, Nashville, Ind.; James A. Mabe, Indianapolis, Ind.; Walter M. Nakatsukasa, Indianapolis, Ind.

[73] Assignee: Eli Lilly and Company, Indianapolis, Ind.

[21] Appl. No.: 452,168

[22] Filed: Dec. 22, 1982

[51] Int. Cl.³ .................. C12N 1/20; C12N 1/00; C12R 1/485; C12R 1/54

[52] U.S. Cl. .................... 435/253; 435/317; 435/889; 435/896; 435/886; 935/29; 935/75; 935/84

[58] Field of Search ............ 435/172, 317, 253

[56] References Cited

U.S. PATENT DOCUMENTS 4,273,875 6/1981 Manis ..................... 435/253
4,332,900 6/1982 Manis et al. ............. 435/172
4,338,400 7/1982 Manis et al. ............. 435/172

FOREIGN PATENT DOCUMENTS 2048894A 12/1980 United Kingdom .

OTHER PUBLICATIONS

Bibb, M. et al., 1980, Developments in Industrial Microbiology 21:55.
Gray O. et al., 1980, Abstracts of the 80th Annual ASM Meeting, Paper No. H68.
International Publication No. WO79/01169.
Bibb, M. et al., 1980, Nature 284:526.
Thompson, C. et al., 1980, Nature 286:525.
Thompson, C. and Cundiffe, E., 1980, J. of Bacteriology 142(2): 455.

Primary Examiner—Alvin E. Tanenholtz
Attorney, Agent, or Firm—Gerald V. Dahling; Arthur R. Whale

[57] ABSTRACT

The present invention discloses selectable recombinant DNA cloning vectors for use in Streptomyces.

57 Claims, 7 Drawing Figures pNM 100 pFJ 143

Restriction Site Map of Plasmids pNM 100 and pFJ 143 pNM 100 pFJ 143

Restriction Site Map of Plasmids
pLR 1, pLR 2 and pLR 4

Restriction Site Map of Plasmids
pFJ 204, pFJ 205, pFJ 206 and pFJ 207

1. pFJ 204 (~5.4 kb)
2. pFJ 205 (~5.4 kb)
3. pFJ 206 (~7.2 kb)
4. pFJ 207 (~7.2 kb)

Restriction Site Map of Plasmids pFJ 208 and pFJ 209

1. pFJ 208 (~8.8 kb)
2. pFJ 209 (~8.8 kb)

Restriction Site Map of Plasmids
pFJ 170, pFJ 210, pFJ 211 and pFJ 212**

1. pFJ 170 (~5.6 kb)
2. pFJ 210 (~5.6 kb)
3. pFJ 211 (~7.4 kb)
4. pFJ 212 (~7.4 kb)

Restriction Site Map of Plasmids
pFJ 213, pFJ 214, pFJ 215 and pFJ 216**

1. pFJ 213 (~9 kb)
2. pFJ 214 (~9 kb)

1. pFJ 215 (~6.5 kb)
2. pFJ 216 (~6.5 kb)

Restriction Site Map of Plasmids pFJ 219 and pFJ 220

1. pFJ 219 (~10 kb)
2. pFJ 220 (~10 kb)

VECTORS FOR CLONING IN STREPTOMYCES

The present invention comprises novel recombinant DNA cloning vectors comprising a functional origin of replication-containing restriction fragment of plasmid pNM100 and one or more DNA segments that confer resistance to antibiotics. The invention further comprises transformants of the aforementioned vectors.

The present invention provides antibiotic resistance-conferring cloning vectors for use in Streptomyces and related host cells. Heretofore, the development and exploitation of recombinant DNA technology in the above organisms has been retarded and made especially difficult because of the general lack of selectable genetic markers on cloning vectors. The vectors of the present invention are functional and selectable in both Streptomyces and other host strains and therefore represent a significant advance in the technical art.

The present vectors are particularly useful because they are small, versatile, and can transform and be selected in any Streptomyces cell that is sensitive to an antibiotic for which resistance is conveyed. Since over half of the clinically important antibiotics are produced by Streptomyces strains, it is desirable to develop cloning systems and vectors that are applicable to that industrially important group. The present invention provides such vectors and thus allows for the cloning of genes into Streptomyces both for increasing the yields of known antibiotics as well as for the production of new antibiotics and antibiotic derivatives.

The present invention provides vehicles for cloning DNA into Streptomyces host cells and also allows for the convenient selection of transformants. Since transformation is a very low frequency event, such a functional test is a practical necessity for determining which cell(s), of among the millions of cells, has acquired the plasmid DNA. This is important because DNA sequences that are non-selectable can be inserted onto the vectors and, upon transformation, cells containing the vector and the particular DNA sequence of interest can be isolated by appropriate antibiotic selection.

For purposes of the present invention as disclosed and claimed herein, the following terms are as defined below.

Recombinant DNA Cloning Vector—any autonomously replicating agent, including but not limited to plasmids, comprising a DNA molecule to which one or more additional DNA segments can or have been added.

Transformation—the introduction of DNA into a recipient host cell that changes the genotype and consequently results in a change in the recipient cell.

Transformant—a recipient host cell that has undergone transformation.

Sensitive Host Cell—a host cell that cannot grow in the presence of a given antibiotic without a DNA segment that confers resistance thereto.

Restriction Fragment—any linear portion or whole of plasmid or chromosomal DNA generated by the action of one or more restriction enzymes.

Insertional Isomer—one of the two or more possible recombinant DNA molecules formed when a DNA fragment is inserted at one of two or more compatible sites on the recipient DNA.

Plasmid pLR2 ~1.6 kb BamHI Restriction Fragment—essentially the same ~1.6 kb BamHI thiostrepton resistance-conferring fragment contained in plasmid pIJ6.

Plasmid pLR1 or pLR4 ~3.4 kb BamHI Restriction Fragment—the same ~3.4 kb BamHI neomycin resistance-conferring fragment contained in plasmid pIJ2.

$Amp^R$—the ampicillin resistant phenotype.
$Tet^S$—the tetracycline sensitive phenotype.
$Thio^R$—the thiostrepton resistant phenotype.
$Neo^R$—the neomycin resistant phenotype.

DETAILED DESCRIPTION OF THE INVENTION

Figure 1:
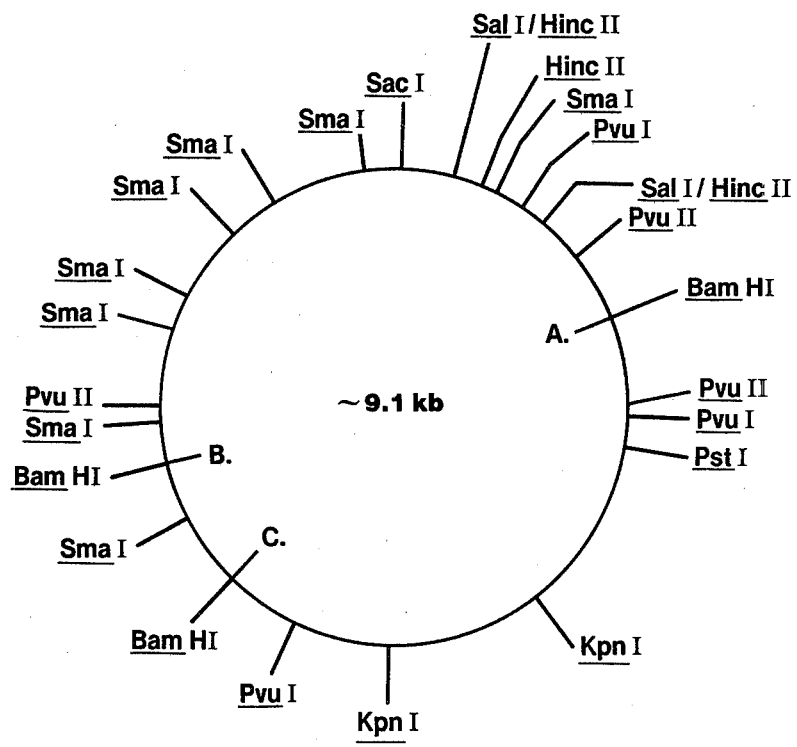
Figure 1:
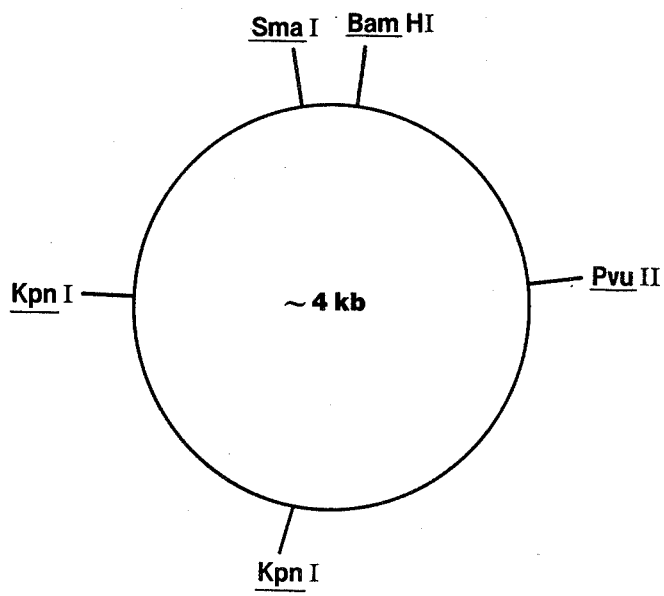

The present invention comprises recombinant DNA cloning vectors comprising:
(a) a functional origin of replication-containing restriction fragment of plasmid pNM100 and
(b) one or more DNA segments that confer resistance to at least one antibiotic when transformed into a sensitive host cell, said host cell being susceptible to transformation, cell division, and culture.

The invention further comprises transformants of the aforementioned vectors.

The vectors of the present invention are constructed by ligating one or more antibiotic resistance-conferring DNA segments into an origin of replication restriction fragment of plasmid pNM100. Plasmid pNM100, from which origin of replication-containing fragments are constructed, is ~9.1 kb and contains several restriction sites which are advantageous for molecular cloning. Since the origin of replication of plasmid pNM100 has been localized to within the ~3.8 kb BamHI restriction fragment, a variety of different origin of replication-containing fragments can be generated by digesting the plasmid with restriction enzymes that cut outside the ~3.8 kb BamHI region. Plasmid pFJ143, an ~4 kb pNM100 derivative from which additional pNM100 origin of replication-containing fragments are obtained, can also be used to construct the present invention. A detailed restriction site map of each of plasmids pNM100 and pFJ143 is presented in FIG. 1 accompanying drawings. For purposes of the present application, FIG. 1 and all subsequent figures are not drawn to scale.

Plasmid pNM100 can be conventionally isolated from Streptomyces virginiae/pNM100, a strain deposited and made part of the permanent stock culture collection of the Northern Regional Research Laboratory, Peoria, Ill. under the accession number NRRL 15156. Plasmid pFJ143 can be conventionally isolated from Streptomyces ambofaciens/pFJ143, a strain similarly deposited under the accession number NRRL 15114. Both strains are available to the public as preferred sources and stock reservoirs of their respective plasmids.

Although many different origin of replication-containing fragments of plasmid pNM100 can be constructed, those exemplified herein for illustrative purposes include the ~3.8 kb BamHI restriction fragment of pNM100 and the ~4 kb BamHI restriction fragment of pFJ143. These fragments can be independently ligated to one or more antibiotic resistance-conferring DNA segments, exemplified herein for illustrative purposes by the thiostrepton resistance-conferring ~1.6 kb BamHI restriction fragment of plasmid pLR2, the neomycin resistance-conferring ~3.4 kb BamHI restriction fragment of plasmid pLR1 or plasmid pLR4 and the erythromycin resistance-conferring ~2.5 kb SalI-BamHI fragment of plasmid pIJ43, to form vectors illustrative of the present invention.

Plasmid pLR2, the source of the thiostrepton resistance-conferring fragment, is ~18.7 kb and is constructed by ligating HindIII-treated plasmid pIJ6, disclosed in Thompson et al., 1980, Nature 286:525, to HindIII-treated plasmid pBR322. Plasmid pLR1, the source of the neomycin resistance-conferring fragment, is ~14.8 kb and is similarly constructed except that plasmid pIJ2, disclosed in Thompson et al., 1980, is substituted for plasmid pIJ6. An analogous construction, resulting in plasmid pLR4, is made by ligating BamHI-treated plasmid pBR322 to BamHI-treated plasmid pLR1. Plasmids pLR2, pLR1 and pLR4 are functional in *E. coli* and therefore can be amplified and isolated conveniently for subsequent manipulation.

Figure 2:
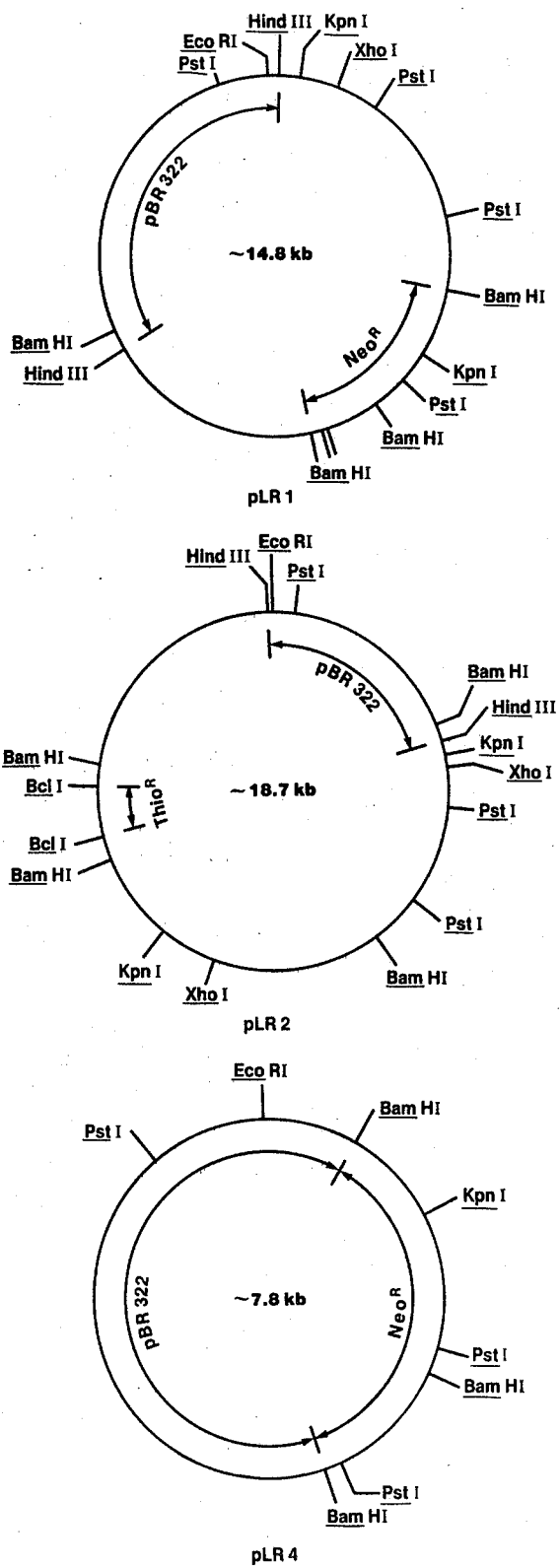

Plasmid pIJ43, the source of the erythromycin resistance-conferring fragment, can be obtained from *E. coli* 803/pIJ43, a strain deposited and made part of the permanent stock culture collection of the American Type Culture Collection, Rockville, Md. It is available to the public as a preferred source and stock reservoir of the plasmid under the accession number ATCC 39156. A restriction site and functional map of each of plasmids pLR1, pLR2 and pLR4 is presented in FIG. 2 of the accompanying drawings.

For convenience and ease of construction, the thiostrepton resistance-conferring ~1.6 kb BamHI fragment, the neomycin resistance-conferring ~3.4 kb BamHI fragment and the erythromycin resistance-conferring ~2.5 kb SalI-BamHI fragment are ligated to the ~3.8 kb origin of replication-containing BamHI fragment of plasmid pNM100 or the ~4 kb origin of replication-containing BamHI fragment of plasmid pFJ143. The resulting recombinant DNA is then ligated to produce plasmids illustrative of the present invention. Recombinant plasmids of two orientations result depending upon the orientation of the particular resistance-conferring DNA fragment. Thus, ligation of the ~1.6 kb BamHI fragment of plasmid pLR2 into the ~3.8 kb BamHI fragment of plasmid pNM100 results in illustrative plasmids pFJ204 and pFJ205; ligation of the ~3.4 kb BamHI fragment of plasmid pLR1 or plasmid pLR4 results in illustrative plasmids pFJ206 and pFJ207; and ligation of both of the fragments results in illustrative plasmids pFJ208 and pFJ209. Similarly, ligation of the ~1.6 kb BamHI fragment into the ~4 kb BamHI fragment of plasmid pFJ143 results in illustrative plasmids pFJ170 and pFJ210; ligation of the ~3.4 kb BamHI fragment results in illustrative plasmids pFJ211 and pFJ212; ligation of both of the ~1.6 kb and ~3.4 kb BamHI fragments results in illustrative plasmids pFJ213 and pFJ214; and ligation of the ~2.5 kb SalI-BamHI fragment with an appropriate linker results in illustrative plasmids pFJ215 and pFJ216.

Various plasmid pNM100 restriction fragments can be used for ligation of the antibiotic resistance-conferring DNA segments provided that the origin of replication contained in the ~3.8 kb BamHI restriction fragment is present. Such plasmid pNM100 restriction fragments include, but are not limited to, the ~9.3 kb BamHI, ~8.4 kb BamHI, ~4.7 kb BamHI, ~9.1 kb SacI, ~5.4 kb SmaI, and ~4.4 kb PvuII fragments. In addition, a particular antibiotic resistance-conferring DNA segment is not limited to a single position but can be ligated or inserted into varying sites of plasmid pNM100 or pFJ143 provided that the origin of replication or other critical plasmid controlled physiological functions are not disrupted. Those skilled in the art understand or can readily determine which sites are advantageous for the ligation or insertion of a particular DNA segment.

Although the thiostrepton, neomycin and erythromycin antibiotic resistance-conferring DNA segments are respectively exemplified by the ~1.6 kb BamHI, ~3.4 kb BamHI, and ~2.5 kb SalI-BamHI restriction fragments of plasmids pLR2, pLR1 and pIJ43, those skilled in the art can construct and use, either individually or in combination, additional DNA segments that also confer resistance to the aforementioned antibiotics. Additional thiostrepton resistance-conferring DNA segments of plasmid pLR2 include, for example, the ~13 kb PstI restriction fragment and also the ~0.8 kb BclI subfragment of the ~1.6 kb BamHI restriction fragment. Additional neomycin resistance-conferring DNA segments of plasmid pLR1 include, for example, the ~3.5 kb PstI restriction fragment and also the larger of the SstI-KpnI subfragments of the ~3.4 kb BamHI restriction fragment. Additional fragments that confer resistance to erythromycin include, for example, the ~2.8 kb SalI, ~2.7 kb SalI-BglII, ~3.0 kb HindIII, ~2.8 kb XhoI-BglII, and the ~4.1 kb EcoRI-BamHI restriction fragments of plasmid pIJ43.

Still other DNA segments that confer resistance to the same or to different antibiotics such as, for example, chloramphenicol, streptomycin, hygromycin, viomycin, tylosin and the like can also be constructed and used by those skilled in the art. In addition, functional derivatives of these or any of the other antibiotic resistance-conferring DNA segments herein described can be constructed by adding, eliminating, or substituting certain nucleotides in accordance with the genetic code. Those skilled in the art will understand that ligation of these derivatives, or any other antibiotic resistance-conferring DNA segment, to a plasmid pNM100 or pFJ143 origin of replication-containing fragment results in vectors that are also within the scope of the present invention.

The restriction fragments of plasmids pNM100 and pFJ143, and also the various antibiotic resistance-conferring DNA segments, can be modified to facilitate ligation. For example, molecular linkers can be provided to either or both of a particular plasmid pNM100 or pFJ143 restriction fragment or a particular resistance-conferring DNA segment. Thus, specific sites for subsequent ligation can be constructed conveniently. In addition, the origin of replication-containing restriction fragments can also be modified by adding, eliminating, or substituting certain nucleotides to provide a variety of restriction sites for ligation of DNA. Those skilled in the art understand nucleotide chemistry and the genetic code and thus which nucleotides are interchangeable and which DNA modifications are desirable for a specific purpose.

The present Streptomyces-functional vectors can also be ligated to a restriction fragment of an *E. coli* plasmid such as, for example, pBR322, pBR324, pBR325, pBR328 and the like, to produce self-replicating vectors that are selectable in both *E. coli* and Streptomyces. These bifunctional constructions comprise the pNM100 origin of replication, a DNA segment that confers antibiotic resistance in Streptomyces, a replicon that is functional in *E. coli* and also a DNA segment that confers antibiotic resistance in *E. coli*. Bifunctional constructions, exemplified herein by plasmids pFJ219 and pFJ220, are particularly advantageous because amplification and manipulation of plasmids can be done faster and more conveniently in *E. coli* than in Streptomyces.

Thus, after desired recombinant DNA procedures are accomplished within the *E. coli* host system, the entire plasmid or the particular Streptomyces DNA can be removed and re-constructed to plasmid form (if necessary), and then transformed into a Streptomyces or related host cell.

The recombinant DNA cloning vectors of the present invention are not limited for use in a single species or strain of Streptomyces. To the contrary, the vectors are broadly applicable and can be transformed into host cells of many Streptomyces taxa, particularly restrictionless strains of economically important taxa that produce antibiotics such as aminoglycoside, macrolide, β-lactam, polyether and glycopeptide antibiotics. Such restrictionless strains are readily selected and isolated from Streptomyces taxa by conventional procedures well known in the art (Lomovskaya et al., 1980, Microbiological Reviews 44:206). Host cells of restrictionless strains lack restriction enzymes and therefore do not cut or degrade plasmid DNA upon transformation. For purposes of the present application, host cells containing restriction enzymes that do not cut any of the restriction sites of the present vectors are also considered restriction-less.

Preferred host cells of restrictionless strains of Streptomyces taxa that produce aminoglycoside antibiotics and in which the present vectors are especially useful and can be transformed, include restrictionless cells of, for example: *S. kanamyceticus* (kanamycins), *S. chrestomyceticus* (aminosidine), *S. griseoflavus* (antibiotic MA 1267), *S. microsporeus* (antibiotic SF-767), *S. ribosidificus* (antibiotic SF733), *S. flavopersicus* (spectinomycin), *S. spectabilis* (actinospectacin), *S. rimosus* forma *paromomycinus* (paromomycins, catenulin), *S. fradiae* var. *italicus* (aminosidine), *S. bluensis* var. *bluensis* (bluensomycin), *S. catenulae* (catenulin), *S. olivoreticuli* var. *cellulophilus* (destomycin A), *S. tenebrarius* (tobramycin, apramycin), *S. lavendulae* (neomycin), *S. albogriseolus* (neomycins), *S. albus* var. *metamycinus* (metamycin), *S. hygroscopicus* var.*sagamiensis* (spectinomycin), *S. bikiniensis* (streptomycin), *S. griseus* (streptomycin), *S. erythrochromogenes* var. *narutoensis* (streptomycin), *S. poolensis* (streptomycin), *S. galbus* (streptomycin), *S. rameus* (streptomycin), *S. olivaceus* (streptomycin), *S. mashuensis* (streptomycin), *S. hygroscopicus* var. *limoneus* (validamycins), *S. rimofaciens* (destomycins), *S. hygroscopicus* forma *glebosus* (glebomycin), *S. fradiae* (hybrimycins neomycins), *S. eurocidicus* (antibiotic A16316-C), *S. aquacanus* (N-methyl hygromycin B), *S. crystallinus* (hygromycin A), *S. noboritoensis* (hygromycin), *S. hygroscopicus* (hygromycins), *S. atrofaciens* (hygromycin), *S. kasugaspinus* (kasugamycins), *S. kasugaensis* (kasugamycins), *S. netropsis* (antibiotic LL-AM31), *S. lividus* (lividomycins), *S. hofuensis* (seldomycin complex), and *S. canus* (ribosyl paromamine).

Preferred host cells of restrictionless strains of Streptomyces taxa that produce macrolide antibiotics and in which the present vectors are especially useful and can be transformed, include restrictionless cells of, for example: *S. caelestis* (antibiotic M188), *S. platensis* (platenomycin), *S. rochei* var. *volubilis* (antibiotic T2636), *S. venezuelae* (methymycins), *S. griseofuscus* (bundlin), *S. narbonensis* (josamycin, narbomycin), *S. fungicidicus* (antibiotic NA-181), *S. griseofaciens* (antibiotic PA133A, B), *S. roseocitreus* (albocycline), *S. bruneogriseus* (albocycline), *S. roseochromogenes* (albocycline), *S. cinerochromogenes* (cineromycin B), *S. albus* (albomycetin), *S. felleus* (argomycin, picromycin), *S. rochei* (lankacidin, borrelidin), *S. violaceoniger* (lankacidin), *S. griseus* (borrelidin), *S. maizeus* (ingramycin), *S. albus* var. *coilmyceticus* (coleimycin), *S. mycarofaciens* (acetyl-leukomycin, espinomycin), *S. hygroscopicus* (turimycin, relomycin, maridomycin, tylosin, carbomycin), *S. griseospiralis* (relomycin), *S. lavendulae* (aldgamycin), *S. rimosus* (neutramycin), *S. deltae* (deltamycins), *S. fungicidicus* var. *espinomyceticus* (espinomycins), *S. furdicidicus* (mydecamycin), *S. ambofaciens* (foromacidin D), *S. eurocidicus* (methymycin), *S. griseolus* (griseomycin), *S. flavochromogenes* (amaromycin, shincomycins), *S. fimbriatus* (amaromycin), *S. fasciculus* (amaromycin), *S. erythreus* (erythromycins), *S. antibioticus* (oleandomycin), *S. olivochromogenes* (oleandomycin), *S. spinichromogenes* var. *suragaoensis* (kujimycins), *S. kitasatoensis* (leucomycin), *S. narbonensis* var. *josamyceticus* (leucomycin A3, josamycin), *S. albogriseolus* (mikonomycin), *S. bikiniensis* (chalcomycin), *S. cirratus* (cirramycin), *S. djakartensis* (niddamycin), *S. eurythermus* (angolamycin), *S. fradiae* (tylosin, lactenocin, macrocin), *S. goshikiensis* (bandamycin), *S. griseoflavus* (acumycin), *S. halstedii* (carbomycin), *S. tendae* (carbomycin), *S. macrosporeus* (carbomycin), *S. thermotolerans* (carbomycin), and *S. albireticuli* (carbomycin).

Preferred host cells of restrictionless strains of Streptomyces taxa that produce β-lactam antibiotics and in which the present vectors are especially useful and can be transformed, include restrictionless cells of, for example: *S. lipmanii* (A16884, MM4550, MM13902), *S. clavuligerus* (A16886B, clavulanic acid), *S. lactamdurans* (cephamycin C), *S. griseus* (cephamycin A, B), *S. hygroscopicus* (deacetoxycephalosporin C), *S. wadayamensis* (WS-3442-D), *S. chartreusis* (SF 1623), *S. heteromorphus* and *S. panayensis* (C2081X); *S. cinnamonensis, S. fimbriatus, S. halstedii, S. rochei* and *S. viridochromogenes* (cephamycins A, B); *S. cattleya* (thienamycin); and *S. olivaceus, S. flavovirens, S. flavus, S. fulvoviridis, S. argenteolus,* and *S. sioyaensis* (MM 4550 and MM 13902).

Preferred host cells of restrictionless strains of Streptomyces taxa that produce polyether antibiotics and in which the present vectors are especially useful and can be transformed, include restrictionless cells of, for example: *S. albus* (A204, A28695A and B, salinomycin), *S. hygroscopicus* (A218, emericid, DE3936), A120A, A286-95A and B, etheromycin, dianemycin), *S. griseus* (grisorixin), *S. conglobatus* (ionomycin), *S. eurocidicus* var. *asterocidicus* (laidlomycin), *S. lasaliensis* (lasalocid), *S. ribosidificus* (lonomycin), *S. cacaoi* var. *asoensis* (lysocellin), *S. cinnamonensis* (monensin), *S. aureofaciens* (narasin), *S. gallinarius* (RP 30504), *S. longwoodensis* (lysocellin), *S. flaveolus* (CP38936), *S. mutabilis* (S-11743a), and *S. violaceoniger* (nigericin).

Preferred host cells of restrictionless strains of Streptomyces taxa that produce glycopeptide antibiotics and in which the present vectors are especially useful and can be transformed, include restrictionless cells of, for example: *S. orientalis* and *S. haranomachiensis* (vancomycin); *S. candidus* (A-35512, avoparcin), and *S. eburosporeus* (LL-AM 374).

Preferred host cells of other Streptomyces restrictionless strains in which the present vectors are especially useful and can be transformed, include restrictionless cells of, for example: *S. coelicolor, S. granuloruber, S. roseosporus, S. lividans, S. tenebrarius, S. espinosus, S. acrimycins, S. glaucescens, S parvilin, S. pristinaespiralis, S. violaceoruber, S. vinaceus, S. virginiae* and *S. azureus.*

In addition to the representative Streptomyces host cells described above, the present vectors are also useful and can be transformed into cells of restrictionless strains of other taxa such as, for example: Bacillus, Staphylococcus and related Actinomycetes, including Streptosporangium, Actinoplanes, Nocardia, and Micromonospora. Thus, the vectors of the present invention have wide application and are useful and can be transformed into host cells of a variety of organisms.

While all the embodiments of the present invention are useful, some of the present recombinant DNA cloning vectors and transformants are preferred. Accordingly, preferred vectors are plasmids pNM100, pFJ204, pFJ207, pFJ208, pFJ143, pFJ170, pFJ212, pFJ214, pFJ215 and pFJ220; and preferred transformants are *Streptomyces ambofaciens*/pNM100, *S. ambofaciens*/pFJ204, *S. lividans*/pFJ204, *S. ambofaciens*/pFJ207, *S. ambofaciens*/pFJ208, *S. ambofaciens*/pFJ143, *S. ambofaciens*/pFJ170, *S. lividans*/pFJ170, *S. ambofaciens*/pFJ212, *S. ambofaciens*/pFJ214, *S. ambofaciens*/pFJ215, *S. ambofaciens*/pFJ220 and *E. coli* K12 HB101/pFJ220. Moreover, of this preferred group, plasmids pNM100, pFJ143, pFJ170, pFJ204, pFJ207 and pFJ208 and transformants *S. ambofaciens*/pNM100, *S. ambofaciens*/pFJ143, *S. ambofaciens*/pFJ170, *S. lividans*/pFJ170, *S. ambofaciens*/pFJ204, *S. ambofaciens*/pFJ207 and *S. ambofaciens*/pFJ208 are most preferred.

The recombinant DNA cloning vectors and transformants of the present invention have broad utility and help fill the need for suitable cloning vehicles for use in Streptomyces and related organisms. Moreover, the ability of the present vectors to confer resistance to antibiotics that are toxic to non-transformed host cells, also provides a functional means for selecting transformants. This is important because of the practical necessity for determining and selecting the particular cells that have acquired vector DNA. Additional DNA segments, that lack functional tests for their presence, can also be inserted onto the present vectors and then transformants containing the non-selectable DNA can be isolated by appropriate antibiotic selection. Such non-selectable DNA segments can be inserted at any site, except within regions necessary for plasmid function and replication, and include, but are not limited to, genes that specify antibiotic modification enzymes and regulatory genes of all types.

More particularly, a non-selectable DNA segment that comprises a gene is inserted on a plasmid such as for example, illustrative plasmid pFJ208, at the central SalI restriction site of the ~1.6 kb BamHI resistance-conferring fragment. Such an insertion inactivates the thiostrepton resistance gene and thus allows for the easy identification of transformants containing the recombinant plasmid. This is done by first selecting for neomycin resistance and, secondarily, identifying those neomycin resistant transformants that are not resistant to thiostrepton. In a similar manner, insertion of a DNA segment of interest at, for example, the internal BamHI restriction site of the ~3.4 kb BamHI resistance-conferring fragment inactivates the neomycin resistance gene. Thus, transformants carrying this recombinant plasmid also are identified easily by first selecting for thiostrepton resistance and, secondarily, identifying those thiostrepton resistant transformants that are not resistant to neomycin. Similar selection involving the insertional inactivation of the erythromycin gene can also be done.

Therefore, the ability to select for antibiotic resistance in Streptomyces and related cells allows for the efficient isolation of the extremely rare cells that contain the particular non-selectable DNA of interest.

The functional test for antibiotic resistance, as described herein above, is also used to locate DNA segments that act as control elements and direct expression of an individual antibiotic resistance gene. Such segments, including but not limited to, promoters, attenuators, repressors, inducers, ribosomal binding sites, and the like, are used to control the expression of other genes in cells of Streptomyces and related organisms.

The thiostrepton, neomycin and erythromycin resistance-conferring vectors of the present invention are also useful for insuring that linked DNA segments are stably maintained in host cells over many generations. These genes or DNA fragments, covalently linked to the thiostrepton, neomycin or erythromycin resistance-conferring fragment and propagated either in Streptomyces or in the cells of related organisms, are maintained by exposing the transformants to levels of thiostrepton, neomycin or erythromycin that are toxic to non-transformed cells. Therefore, transformants that lose the vector, and consequently any covalently linked DNA, cannot grow and are eliminated from the culture. Thus, the vectors of the present invention can stabilize and maintain any DNA sequence of interest.

The cloning vectors and transformants of the present invention provide for the cloning of genes to improve yields of various products that are currently produced in Streptomyces and related cells. Examples of such products include, but are not limited to, Streptomycin, Tylosin, Cephalosporins, Actaplanin, Narasin, Monensin, Apramycin, Tobramycin, Erythromycin, Tetracycline, Chloramphenicol, and the like. The present invention also provides selectable vectors that are useful for cloning, characterizing and reconstructing DNA sequences that code for commercially important proteins such as, for example, human insulin, human proinsulin, glucagon, interferon, human growth hormone, bovine growth hormone and the like; for enzymatic functions in metabolic pathways leading to commercially important processes and compounds; or for control elements that improve gene expression. These desired DNA sequences include, but are not limited to, DNA that codes for enzymes that catalyze synthesis of derivatized antibiotics such as, for example, Streptomycin, Cephalosporin, Tylosin, Actaplanin, Narasin, Monensin, Apramycin, Tobramycin, Tetracycline, Chloramphenicol and Erythromycin derivatives, or for enzymes that mediate and increase bioproduction of antibiotics or other products. The capability for inserting and stabilizing such DNA segments thus allows for increasing the yield and availability of antibiotics that are produced by Streptomyces and related organisms.

*Streptomyces virginiae*/pNM100 and *S. ambofaciens*/pFJ143, respective sources of plasmids pNM100 and pFJ143, can be cultured in a number of ways using any of several different media. Carbohydrate sources which are preferred in a culture medium include, for example, molasses, glucose, dextrin and glycerol, and nitrogen sources include, for example, soy flour, amino acid mixtures and peptones. Nutrient inorganic salts are also incorporated and include the customary salts capable of yielding sodium, potassium, ammonia, calcium, phosphate, chloride, sulfate and like ions. As is necessary for the growth and development of other microorganisms, essential trace elements are also added. Such trace elements are commonly supplied as impurities incidental to the addition of other constituents of the medium.

*Streptomyces virginiae*/pNM100 and *S. ambofaciens*/pFJ143 are grown under aerobic culture conditions over a relatively wide pH range of about 5 to 9 at temperatures ranging from about 15° to 40° C. For production of plasmids pNM100 and pFJ143 in greatest quantity, however, it is desirable to start with a culture medium at a pH of about 7.2 and maintain a culture temperature of about 30° C. Culturing *Streptomyces virginiae*/pNM100 and *S. ambofaciens*/pFJ143 under the aforementioned conditions results in a reservoir of cells from which plasmids pNM100 and pFJ143 can be isolated by techniques well known in the art.

The following examples further illustrate and detail the invention disclosed herein. Both an explanation of and the actual procedures for constructing the invention are described where appropriate.

EXAMPLE 1

Isolation of Plasmid pNM100

A. Culture of *Streptomyces virginiae*/pNM100

A vegetative inoculum of *Streptomyces virginiae*/pNM100 (NRRL 15156) was conventionally prepared by growing the strain under submerged aerobic conditions in 50 ml. of sterilized trypticase soy broth* at 35 g./l in deionized water.

*Trypticase soy broth is obtained from Difco Laboratories, Detroit, Mich.

The trypticase soy broth inoculum was incubated for 48 hours at a temperature of 30° C. About 10 ml. of the incubated inoculum were first transferred to 500 ml. of sterilized broth and then incubated for about 20 hours at 30° C. The pH was not adjusted. After incubation, the *Streptomyces virginiae*/pNM100 cells were ready for harvest and subsequent isolation of plasmid DNA.

B. Plasmid Isolation

About 10 g. (wet wgt) of *Streptomyces virginiae*/pNM100 cells were harvested by centrifugation (10 minutes, 5° C., 10,000 rpm). The cells were homogenized using a tissue grinder, washed in TES buffer (0.05 M tris(hydroxymethyl)aminomethane [tris], 0.005 M EDTA, and 0.05 M NaCl, pH 8.0), and then suspended in TES buffer containing 25% sucrose. After the addition of about 120 mg. of lysozyme in 20 ml. of TES-25% sucrose buffer, the suspension was incubated at 35°–37° C. for about 20 minutes and, upon addition of 40 ml. of 0.25 M EDTA, pH 8.0, the suspension was again incubated at 35° C. for 10 minutes. Following this, about 40 ml. of 5% SDS (sodium dodecyl sulfate) in TE buffer (0.01 M tris, 0.001 M EDTA, pH 8.0) was added and then, after the resultant mixture was again incubated at 35°–37° C. for 20 minutes, about 50 ml. of 5 M NaCl in deionized water was added. The mixture was stirred, placed on an ice bath for about 4 hours and then centrifuged (30 minutes, 4° C., 10,000 rpm). About 0.313 volumes of 42% polyethylene glycol in deionized water were added to the NaCl supernatant and the resulting mixture was cooled at 4° C. for about 18 hours. The DNA precipitate was collected by centrifugation (5 minutes, 4° C., 3000 rpm) and was then dissolved in TES buffer at pH 8.0. Centrifugation (40 hours, 15° C., 35,000 rpm) using cesium chloride and ethidium chloride gradients separated the DNA into two well defined bands with the lower band constituting the desired plasmid pNM100. As an alternative, 4.14 g. cesium chloride can be dissolved in 1.84 ml. of STE (10 mM Tris-HCl, pH 8, 10 mM NaCl, 1 mM EDTA, pH 8) and 0.5 ml. EDTA (0.25 M, pH 8). About 1 ml. DNA suspension and 0.8 ml. ethidium bromide (5 mg./ml.) are added resulting in a 5.1 ml. gradient with 1.6 g./ml. cesium chloride and 800 µg./ml. ethidium bromide. Centrifugation (5 hours, 20° C., 60,000 r.p.m.) in an ultracentrifuge with a vertical rotor, such as Beckman VTi65, followed by deceleration for ~1.3 hours without breaking, results in well defined bands. The lower band constitutes the desired plasmid pNM100. Following conventional procedures, the plasmid band was removed, washed twice with isoamyl alcohol, dialyzed over TE buffer at pH 8.0 and precipitated with ethanol. The thus isolated plasmid pNM100 DNA was dissolved in 0.4 ml. of TE buffer at pH 8.0, and was then frozen at −20° C. for storage.

EXAMPLE 2

Construction of Plasmid pLR2

A. HindIII Digestion of Plasmid pIJ6

About 20 µl. (20 µg.) of plasmid pIJ6 DNA, disclosed in Thompson et al., 1980, Nature 286:525, 5 µl. BSA(-Bovine Serum albumin, 1 mg./ml.), 19 µl. water, 1 µl. of HindIII (containing 3 New England Bio Labs units) restriction enzyme*, and 5 µl. reaction mix** were incubated at 37° C. for 2 hours. The reaction was terminated by the addition of about 50 µl. of 4 M ammonium acetate and 200 µl. of 95% ethanol. The resultant DNA precipitate was washed twice in 70% ethanol, dried in vacuo, suspended in 20 µl. of TE buffer, and frozen at −20° C. for storage.

*Restriction enzymes can be obtained from the following sources:
New England Bio Labs., Inc. 32 Tozer Road Beverly, Mass. 01915
Boehringer-Mannheim Biochemicals 7941 Castleway Drive Indianapolis, Ind. 46250
Bethesda Research Laboratories Inc. P.O. Box 577, Gaithersburg, Md. 20760

**Reaction mix for HindIII restriction enzyme was prepared with the following composition.
600 mM NaCl
100 mM Tris-HCl, pH 7.9
70 mM $MgCl_2$
10 mM Dithiothreitol

B. HindIII Digestion of Plasmid pBR322

About 8 µl. (4 µg.) of plasmid pBR322 DNA, 5 µl. mix, 5 µl. (1 mg./ml.), 31 µl. water, and 1 µl. of HindIII restriction enzyme were incubated at 37° C. for 2 hours. After the reaction was terminated by incubating at 60° C. for 10 minutes, about 50 µl. of 4 M ammonium acetate and 200 µl. 95% ethanol were added. The resultant DNA precipitate was washed twice in 70% ethanol, dried in vacuo, and suspended in 45 µl. of water.

C. Ligation of HindIII Digested Plasmids pIJ6 and pBR322

About 20 µl. of HindIII treated plasmid pIJ6 (from Example 2A), 20 µl. of HindIII treated plasmid pBR322 (from Example 2B), 5 µl. BSA (1 mg./ml.), 1 µl. of T4 DNA ligase*, and 5 µl. ligation mix** were incubated at 16° C. for 4 hours. The reaction was terminated by the addition of about 50 µl. 4 M ammonium acetate and 200 µl. of 95% ethanol. The resultant DNA precipitate was washed twice in 70% ethanol, dried in vacuo, and suspended in TE buffer. The suspended DNA constituted the desired plasmid pLR2.

*T4 DNA ligase can be obtained from the following source:
New England Bio Labs., Inc. 32 Tozer Rd. Beverly, Mass. 01915
**Ligation mix was prepared with the following composition.
500 mM Tris-HCl, pH 7.8

200 mM Dithiothreitol
100 mM MgCl$_2$
10 mM ATP

EXAMPLE 3

Construction of E. coli K12 HB101/pLR2

About 10 ml. of frozen competent E. coli K12 HB101 cells (Bolivar et al., 1977, Gene 2:75-93) were pelleted by centrifugation and then suspended in about 10 ml. of 0.01 M sodium chloride. Next, the cells were pelleted again, resuspended in about 10 ml. of 0.03 M calcium chloride, incubated on ice for 20 minutes, pelleted a third time, and finally, resuspended in 1.25 ml. of 0.03 M calcium chloride. The resultant cell suspension was competent for subsequent transformation.

Plasmid pLR2 in TE buffer (prepared in Example 2C) was ethanol precipitated, suspended in 150 $\mu$l. of 30 mM calcium chloride solution, and gently mixed in a test tube with about 200 $\mu$l. of competent E. coli K12 HB101 cells. The resultant mixture was incubated on ice for about 45 minutes and then at 42° C. for about 1 minute. Next, about 3 ml. of L-broth (Bertani, 1951, J. Bacteriology 62:293) containing 50 $\mu$g./ml. of ampicillin was added. The mixture was incubated with shaking at 37° C. for 1 hour and then plated on L-agar (Miller, 1972, Experiments in Molecular Genetics, Cold Spring Harbor Labs, Cold Spring Harbor, N.Y.) containing ampicillin. Surviving colonies were selected and tested for the expected phenotype ($Amp^R$, $Tet^S$), and constituted the desired E. coli K12 HB101/pLR2 transformants.

EXAMPLE 4

Construction of Plasmid pLR1

Plasmid pLR1 was prepared in substantial accordance with the teaching of Example 2A-C except that plasmid pIJ2, disclosed in Thompson et al., 1980, Nature 286:525, was used in place of plasmid pIJ6. The desired plasmid pLR1 was suspended in TE buffer.

EXAMPLE 5

Construction of E. coli K12 HB101/pLR1.

The desired construction was carried out in substantial accordance with the teaching of Example 3 except that plasmid pLR1, rather than plasmid pLR2, was used for transformation. Surviving colonies were selected and tested for the expected phenotype ($Amp^R$, $Tet^S$), and constituted the desired E. coli K12 HB101/pLR1 transformants.

EXAMPLE 6

Construction of Plasmid pLR4 A. Partial BamHI Digestion of Plasmid pLR1.

About 10 $\mu$l. (10 $\mu$g.) of plasmid pLR1, 5 $\mu$l. BSA (1 mg./ml.), 29 $\mu$l. water, 1 $\mu$l. of BamHI (diluted 1:4 with water) restriction enzyme, and 5 $\mu$l. reaction mix* were incubated at 37° C. for 15 minutes. The reaction was terminated by the addition of about 50 $\mu$l. of 4M ammonium acetate and 200 $\mu$l. of 95% ethanol. The resultant DNA precipitate was washed twice in 70% ethanol, dried in vacuo, and suspended in 20 $\mu$l. water.
*Reaction mix for BamHI restriction enzyme was prepared with the following composition.

1.5 M NaCl
60 mM Tris-HCl, $p^H$ 7.9
60 mM MgCl$_2$

B. BamHI Digestion of Plasmid pBR322

The desired digestion was carried out in substantial accordance with the teaching of Example 2B except that BamHI restriction enzyme was used in place of HindIII restriction enzyme. The digested plasmid pBR322 was suspended in 29 $\mu$l. of water.

C. Ligation of Partial BamHI Digested Plasmid pLR1. and Bam HI Digested Plasmid pBR322

The desired ligation was carried out in substantial accordance with the teaching of Example 2C. The resultant ligated DNA was suspended in TE buffer and constituted the desired plasmid pLR4.

EXAMPLE 7

Construction of E. coli K12 HB101/pLR4

The desired construction was carried out in substantial accordance with the teaching of Example 3 except that plasmid pLR4, rather than plasmid pLR2, was used for transformation. Surviving colonies were selected and tested for the expected phenotype ($Amp^R$, $Tet^S$), and constituted the desired E. coli K12 HB101/pLR4 transformants.

EXAMPLE 8

Construction of Plasmids pFJ204 and pFJ205

A. BamHI Digestion of Plasmid pLR2 and Isolation of the ~1.6 kb Thiostrepton Resistance-Conferring Fragment About 50 $\mu$g. of plasmid pLR2 DNA, 10 $\mu$l reaction mix, 10 $\mu$l. BSA (1 mg./ml.), 29 $\mu$l. water, and 1 $\mu$l. (4 units/$\mu$l.) of BamHI restriction enzyme are incubated at 37° C. for 2 hours. After adding an equal volume of 4 M ammonium acetate and 2.5 volumes of 95% ethanol, the mixture is cooled at $-20°$ C. for about 18 hours to precipitate the DNA. The DNA precipitate is collected by centrifugation and then suspended in about 50 $\mu$l. of TE buffer. The desired ~1.6 kb BamHI restriction fragment is isolated conventionally from the DNA suspension by agarose gel electrophoresis in substantial accordance with the teaching of Davis, R. W. et al., 1980, A Manual For Genetic Engineering, Advanced Bacteriol Genetics, Cold Spring Harbor Laboratories, Cold Spring Harbor, N.Y. Following isolation, the fragment is resuspended in about 20 $\mu$l. of TE buffer for subsequent ligation.

B. BamHI Digestion of Plasmid pNM100 and Isolation of the ~3.8 kb Origin of Replication-Containing Fragment The desired digestion and isolation are carried out in substantial accordance with the teaching of Example 8A except that plasmid pNM100, rather than plasmid pLR2, is used. Following isolation, the ~3.8 kb fragment is suspended in about 50 $\mu$l. of TE buffer for subsequent ligation.

C. Ligation

About 1 $\mu$g. of the ~3.8 kb BamHI fragment of plasmid pNM100, 1 $\mu$g. of the ~1.6 kb BamHI restriction fragment of plasmid pLR2, 5 $\mu$l. ligation mix, 5 $\mu$l. BSA (1 mg./ml.), 25 $\mu$l. water, and 5 $\mu$l. T4 DNA ligase (New England Bio Labs) are incubated at about 16° C. for about 4 hours. After adding about 50 $\mu$l. of 4 M ammonium acetate and about 300 $\mu$l. of cold ethanol, the mixture is cooled to about −20° C. for about 18 hours to precipitate the DNA. The DNA precipitate is collected by centrifugation, washed with 70% ethanol, collected again, and then suspended in 50 μl. of medium P (Hopwood and Wright 1978, J. Molecular and General Genetics 162:307) for subsequent transformation.

Figure 3:
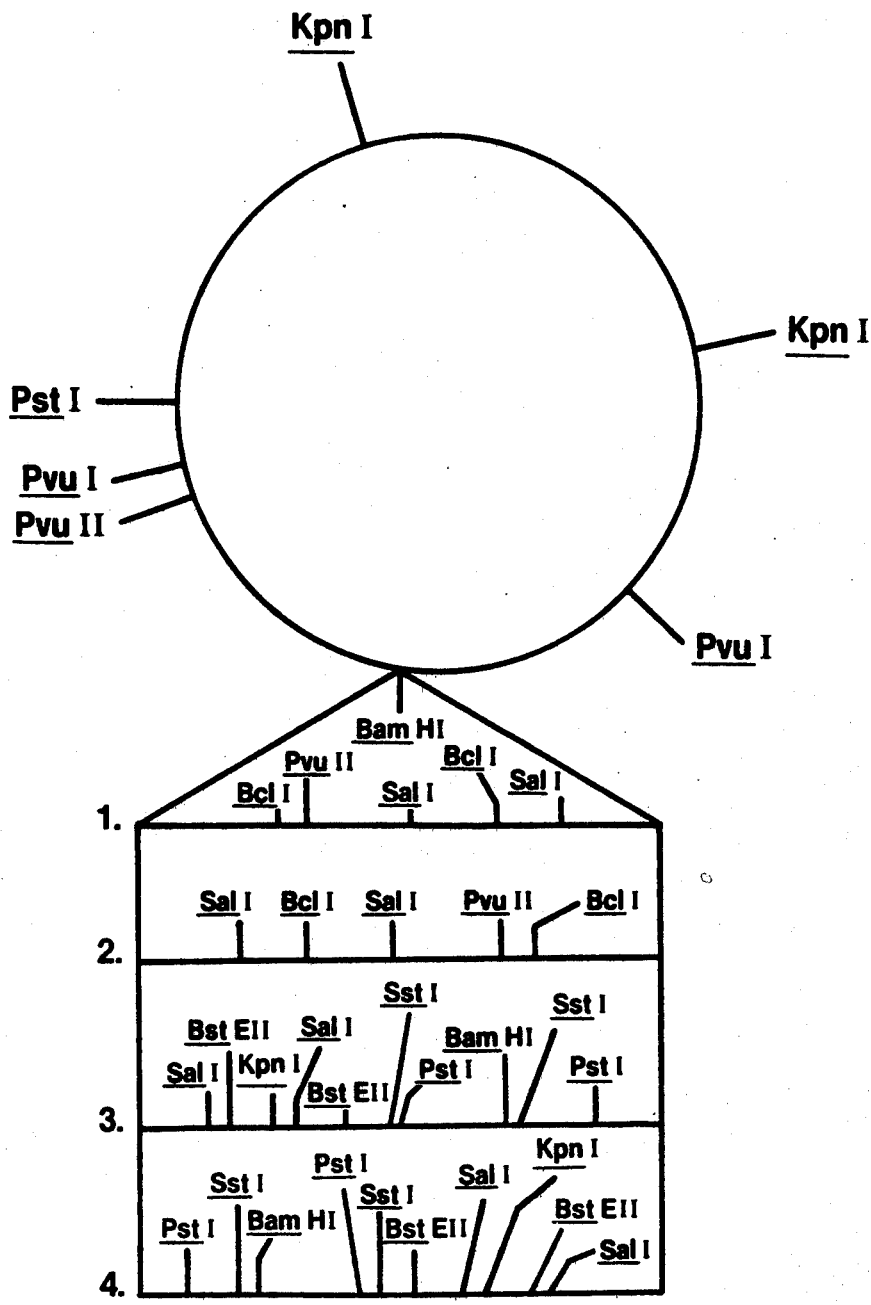

Recombinant plasmids of two orientations result because the ~1.6 kb BamHI resistance-conferring fragment can be oriented in either direction. The resultant plasmids pFJ204 and pFJ205 can be transformed into appropriate host cells and then conventionally, identified by restriction enzyme and agarose gel electrophoretic analysis (Davis, R. W. et al. 1980). A restriction site and functional map of each of plasmids pFJ204 and pFJ205 is presented in FIG. 3 of the accompanying drawings.

EXAMPLE 9

Construction of *Streptomyces ambofaciens*/pFJ204 and *S. ambofaciens*/pFJ205

Using about 1 μg. of the DNA from Example 8C and 1×10⁸ protoplasts of *Streptomyces ambofaciens*, a strain deposited and made part of the permanent stock culture collection of the Northern Regional Research Laboratory, Peoria, Ill. from which it is available to the public under the accession number NRRL 2420, the desired constructions are made in substantial accordance with the teaching of International Publication (of International patent application No. PCT/GB79/00095) No. WO79/01169, Example 2. The desired transformants are selected for thiostrepton resistance by overlaying the regenerating protoplasts with R2 medium (Hopwood and Wright, 1978, Molecular and General Genetics 162:30) top agar containing sufficient thiostrepton to bring the final plate concentration to 50 μg./ml. The resultant *Streptomyces ambofaciens*/pFJ204 and *S. ambofaciens*/pFJ205 thiostrepton resistant colonies are isolated according to known procedures, cultured, and then conventionally identified by restriction enzyme and agarose gel electrophoretic analysis of the constitutive plasmids (Davis, R. W. et al., 1980). The transformant cultures are then used for subsequent production and isolation of their respective plasmids.

EXAMPLE 10

Construction of Plasmids pFJ206 and pFJ207

A. BamHI Digestion of Plasmid pLR1 and Isolation of the ~3.4 kb Neomycin Resistance-Conferring Fragment The desired digestion and isolation are carried out in substantial accordance with the teaching of Example 8A. The ~3.4 kb BamHI restriction fragment is suspended in about 20 μl. of TE buffer for subsequent ligation.

B. Ligation

The ~3.4 kb BamHI neomycin resistance-conferring restriction fragment is ligated to the ~3.8 kb BamHI fragment of plasmid pNM100 (prepared in Example 8B) in substantial accordance with the teaching of Example 8C.

Recombinant plasmids of two orientations result because the ~3.4 kb BamHI resistance-conferring fragment can be oriented in either direction. The resultant plasmids pFJ206 and pFJ207 can be transformed into appropriate host cells and then conventionally identified by restriction enzyme and agarose gel electrophoretic analysis (Davis, R. W. et al., 1980). A restriction site and functional map of each of plasmids pFJ206 and pFJ207 is presented in FIG. 3 of the accompanying drawings.

EXAMPLE 11

Construction of *Streptomyces ambofaciens*/pFJ206 and *S. ambofaciens*/pFJ207

Using about 1 μg. of the DNA from Example 10 and 1×10⁸ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected for neomycin resistance by overlaying the regenerating protoplasts with R2 medium top agar containing sufficient neomycin* to bring the final plate concentration to 1 μg./ml.

*Antibiotic neomycin can be obtained from Sigma, St. Louis, MO.

The resultant *Streptomyces ambofaciens*/pFJ206 and *S. ambofaciens*/pFJ207 neomycin resistant colonies are isolated according to known procedures and then conventionally identified by restriction enzyme and electrophoretic analysis of the constitutive plasmids (Davis, R. W. et al., 1980). The transformant cultures are then used for subsequent production and isolation of their respective plasmids.

EXAMPLE 12

Construction of Plasmids pFJ208 and pFJ209

Plasmid pFJ204, isolated from *Streptomyces ambofaciens*/pFJ204 according to the procedure of Example 1, is partially digested with BamHI restriction enzyme. The digestion is carried out by incubating about 20 μg. of plasmid pFJ204 DNA, 10 μl. reaction mix, 10 μl. BSA (1 mg./ml.), 39 μl. water, and 1 μl. of BamHI restriction enzyme (prepared by diluting 2 μl. of enzyme in 8 μl. of water) at ambient temperature for about 15 minutes. After adding an equal volume of 4 M ammonium acetate and 5 volumes of 95% ethanol, the mixture is cooled at −20° C. for about 18 hours to precipitate the DNA. The DNA precipitate is collected by centrifugation, rinsed in 70% ethanol, dried in vacuo, and then suspended in about 50 μl. of TE buffer.

Figure 4:
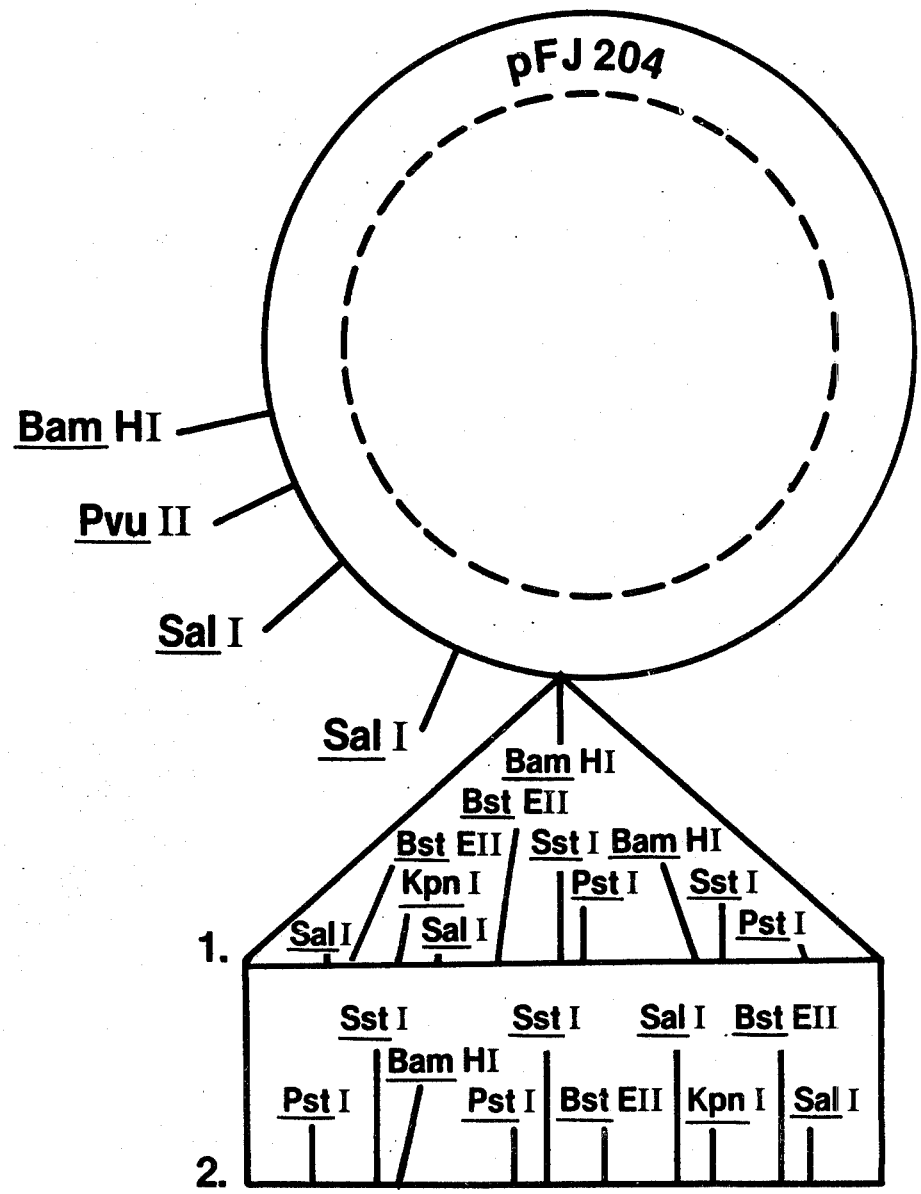

The partial BamHI digest is then ligated, in substantial accordance with the teaching of Example 8C, to the plasmid pLR1 ~3.4 kb neomycin resistance-conferring BamHI fragment (prepared in Example 10A), to produce the desired plasmids. The insertional isomers of plasmids pFJ208 and pFJ209 are also produced since plasmid pFJ204 has two BamHI restriction sites for the insertion of the neomycin resistance fragment. Recombinant plasmids of two orientations result because the ~3.4 kb BamHI neomycin resistance-conferring fragment can be oriented in either direction. The resultant plasmids pFJ208 and pFJ209 can be transformed into appropriate host cells and then conventionally identified by restriction enzyme and agarose gel electrophoretic analysis (Davis, R. W., et al., 1980). A restriction site and functional map of each of plasmids pFJ208 and pFJ209 is presented in FIG. 4 of the accompanying drawings.

EXAMPLE 13

Construction of *Streptomyces ambofaciens*/pFJ208 and *S. ambofaciens*/pFJ209

Using 1 μg. of the DNA from Example 12 and $1 \times 10^8$ protoplasts of *Streptomyces ambofaciens* (NRRL No. 2420), the desired constructions are made in substantial accordance with the teaching of International Publication (of International patent application No. PCT/GB79/00095) No. WO79/01169, Example 2. The desired transformants are selected first for thiostrepton resistance and then for neomycin resistance by the methods described in Examples 9 and 11 above. The resultant *Streptomyces ambofaciens*/pFJ208 and *S. ambofaciens*/pFJ209 thiostrepton and neomycin resistant colonies are isolated according to known procedures and then conventionally identified by restriction enzyme and electrophoretic analysis of the constitutive plasmids (Davis, R. W. et al., 1980). The transformant cultures are then used for subsequent production and isolation of their respective plasmids.

EXAMPLE 14

Isolation of Plasmid pFJ143

A. Culture of Streptomyces ambofaciens/pFJ143

A vegetative inoculum of *Streptomyces ambofaciens*/pFJ143 (NRRL 15114) was conventionally prepared in substantial accordance with the teaching of Example 1A.

B. Plasmid Isolation

The desired isolation was carried out in substantial accordance with the teaching of Example 1B except that the inoculum of Example 14A, rather than the inoculum of Example 1A, was used. The isolated plasmid pFJ143 DNA was dissolved in 1 ml. of 10 fold diluted TE buffer and was then frozen at −20° C. for storage.

EXAMPLE 15

Construction of Plasmids pFJ170 and pFJ210

A. BamHI Digestion of Plasmid pFJ143

The desired digestion is carried out in substantial accordance with the teaching of Example 8A except that plasmid pFJ143, rather than plasmid pLR2, is used. The DNA precipitate was collected by centrifugation, rinsed in 70% ethanol, dried in vacuo, and then suspended in about 50 μl. of TE buffer.

B. Ligation

Figure 5:
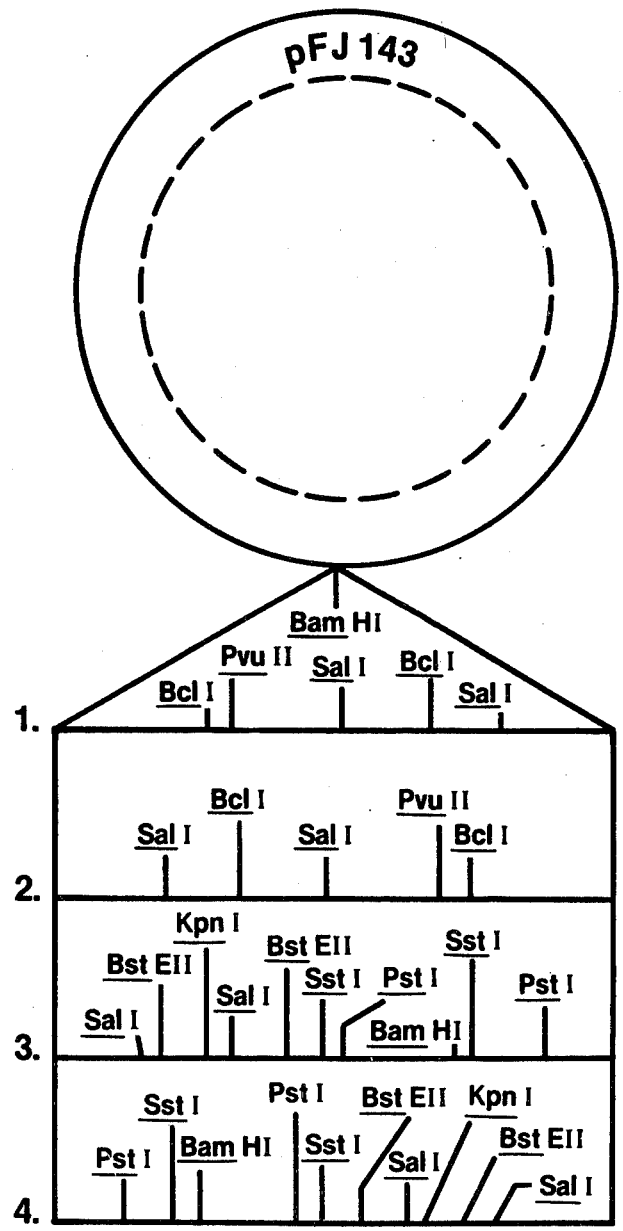

About 1 μg. of the BamHI digested plasmid pFJ143 and 1 μg. of the ~1.6 kb BamHI restriction fragment of plasmid pLR2 (prepared in Example 8A) were ligated in substantial accordance with the teaching of Example 8C. Recombinant plasmids of two orientations result because the ~1.6 kb BamHI resistance-conferring fragment can be oriented in either direction. The resultant plasmids pFJ170 and pFJ210 can be transformed into appropriate host cells and then conventionally identified by restriction enzyme and agarose gel electrophoretic analysis (Davis, R. W. et al., 1980). A restriction site and functional map of each of plasmids pFJ170 and pFJ210 is presented in FIG. 5 of the accompanying drawings.

EXAMPLE 16

Construction of *Streptomyces ambofaciens*/pFJ170 and *S. ambofaciens*/pFJ210

With the exception that DNA from Example 15C is used, the desired constructions are made, conventionally identified and used for subsequent production and isolation of plasmids pFJ170 and pFJ210 in substantial accordance with the teaching of Example 9.

EXAMPLE 17

Construction of Plasmids pFJ211 and pFJ212

The desired constructions are made and conventionally identified in substantial accordance with the teaching of Example 10 except that BamHI digested plasmid pFJ143, rather than the ~3.8 kb BamHI fragment of plasmid pNM100, is used. A restriction site and functional map of each of plasmids pFJ211 and pFJ212 is presented in FIG. 5 of the accompanying drawings.

EXAMPLE 18

Construction of *Streptomyces ambofaciens*/pFJ211 and *S. ambofaciens*/pFJ212

With the exception that DNA from Example 17 is used, the desired constructions are made, conventionally identified and used for subsequent production and isolation of plasmids pFJ211 and pFJ212 in substantial accordance with the teaching of Example 11.

EXAMPLE 19

Construction of Plasmids pFJ213 and pFJ214

Figure 6:
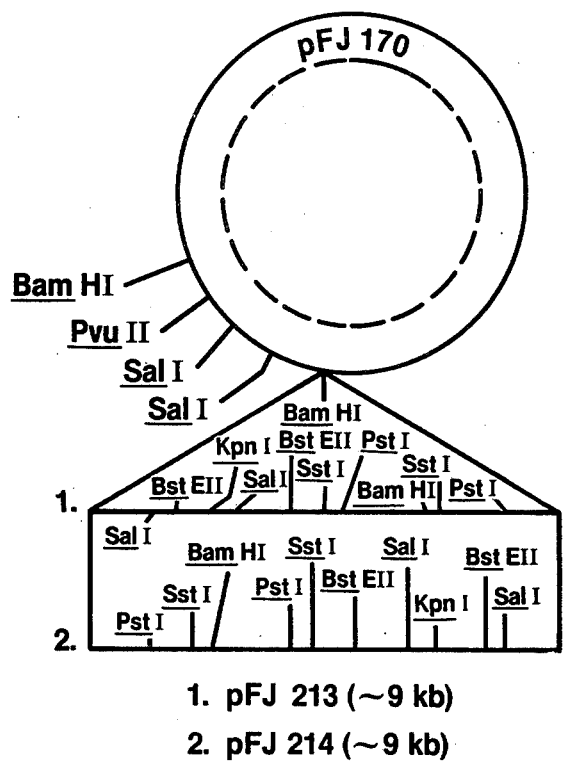
Figure 6:
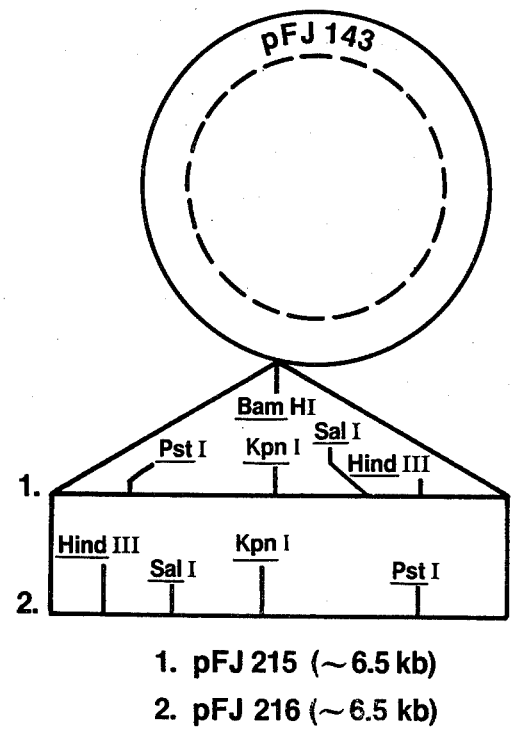

The desired constructions are made and conventionally identified in substantial accordance with the teaching of Example 12 except that plasmid pFJ170, rather than plasmid pFJ204, is used. The insertional isomers of plasmids pFJ213 and pFJ214 are also produced since plasmid pFJ170 has two BamHI restriction sites for the insertion of the neomycin resistance fragment. Recombinant plasmids of two orientations result because the ~3.4 kb BamHI neomycin resistance-conferring fragment can be oriented in either direction. A restriction site and functional map of each of plasmids pFJ213 and pFJ214 is presented in FIG. 6 of the accompanying drawings.

EXAMPLE 20

Construction of *Streptomyces ambofaciens*/pFJ213 and *S. ambofaciens*/pFJ214

With the exception that DNA from Example 19 is used, the desired constructions are made, conventionally identified and used for subsequent production and isolation of plasmids pFJ213 and pFJ214 in substantial accordance with the teaching of Example 13.

EXAMPLE 21

Construction of Plasmids pFJ215 and pFJ216

A. Culture of E. coli 803/pIJ43 and Isolation of Plasmid pIJ43

The desired culturing of *E. coli* 803/pIJ43 (ATCC 39156) and the subsequent isolation of plasmid pIJ43 are both carried out in substantial accordance with the teaching of Davis, R. W. et al., 1980. The pIJ43 DNA is conventionally suspended in TE buffer and then cooled to −20° C. for storage.

B. Digestion and Isolation of ~2.5 kb SalI-BamHI Fragment of plasmid pIJ43

About 20 μg. of plasmid pIJ43 DNA, 10 μl. reaction mix*, 10 μl. BSA (1 mg./ml.) 39 μl. water, and 1 μl. of SalI restriction enzyme (prepared by diluting in such a manner that 1 μl. contains 60 New England Bio Labs Units) were incubated at ambient temperature for about 15 minutes. After adding an equal volume of 4 M ammonium acetate and 2 volumes of 95% ethanol, the mixture was cooled at −20° C. for about 18 hours to precipitate the DNA. The DNA precipitate was collected by centrifugation, rinsed in 70% ethanol, dried in vacuo, and then suspended in about 20 μl. of TE buffer. Following addition of about 5 μl. of BamHI reaction mix, 5 μl. BSA (1 mg./ml.), 39 μl. water, and 1 μl. of BamHI restriction (containing excess New England Bio Lab units), the mixture was incubated at 37° C. for about 60 minutes. An equal volume of 4 M ammonium acetate and 2 volumes of 95% ethanol were added and then the mixture was cooled at −20° C. for about 18 hours to precipitate the DNA. The DNA precipitate was collected by centrifugation. The desired ~2.5 kb SalI-BamHI fragments are separated and isolated conventionally by agarose gel electrophoresis (Davis, R. W. et al., 1980).

*Reaction mix for SalI restriction enzyme was prepared with the following composition.
1.5 M NaCl
60 mMTris-HCl, pH 7.9
60 mM MgCl$_2$
60 mM 2-mercaptoethanol

C. Addition of BamHI Linkers to the ~2.5 kb SalI-BamHI Fragment of Plasmid pIJ43

The addition of BamHI linkers* is carried out in substantial accordance with the teaching of Ullrich et al., 1977, Science 196:1313. The resultant fragment is treated with BamHI restriction enzyme to produce the desired BamHI sticky termini. The ~2.5 kb BamHI fragment is then isolated according to known procedures and stored for subsequent ligation.

*BamHI[d(CGGATCCG)] and other linkers are readily available at: Collaborative Research Inc. 128 Spring St. Lexington, Mass. 02173

D. Ligation

About 1 μg. of BamHI digested plasmid pFJ143 (prepared in Example 15A) and 1 μg. of the ~2.5 kb fragment of plasmid pIJ43 (prepared in Examples 21B and C), are ligated in substantial accordance with the teaching of Example 8C. Recombinant plasmids of two orientations result because the ~2.5 kb BamHI fragment can be oriented in either direction. The resultant plasmids pFJ215 and pFJ216 can be transformed into appropriate host cells and then conventionally identified by restriction enzyme and agarose gel electrophoretic analyses (Davis, R. W. et al., 1980). A restriction site and functional map of each of plasmids pFJ215 and pFJ216 is presented in FIG. 6 of the accompanying drawings.

EXAMPLE 22

Construction of *Streptomyces ambofaciens*/pFJ215 and *S. ambofaciens*/pFJ216

The desired constructions are made in substantial accordance with the teaching of Example 9 except that plasmid pFJ215 and pFJ216 DNA, rather than DNA from Example 8C, is used. The desired transformants are selected for erythromycin resistance by overlaying the regenerating protoplasts with R2 medium top agar containing sufficient erythromycin to bring the plate concentration to 50 μg./ml. The resultant *Streptomyces ambofaciens*/pFJ215 and *S. ambofaciens*/-pFJ216 erythromycin resistant colonies are isolated according to known procedures, cultured, tested for thiostrepton resistance and then conventionally identified by restriction enzyme and agarose gel electrophoretic analysis of the constitutive plasmids. The desired transformants are then conventionally cultured for subsequent production and isolation of plasmids pFJ215 and pFJ216.

EXAMPLE 23

Construction of Chimeric Plasmids pFJ219 and pFJ220

Figure 7:
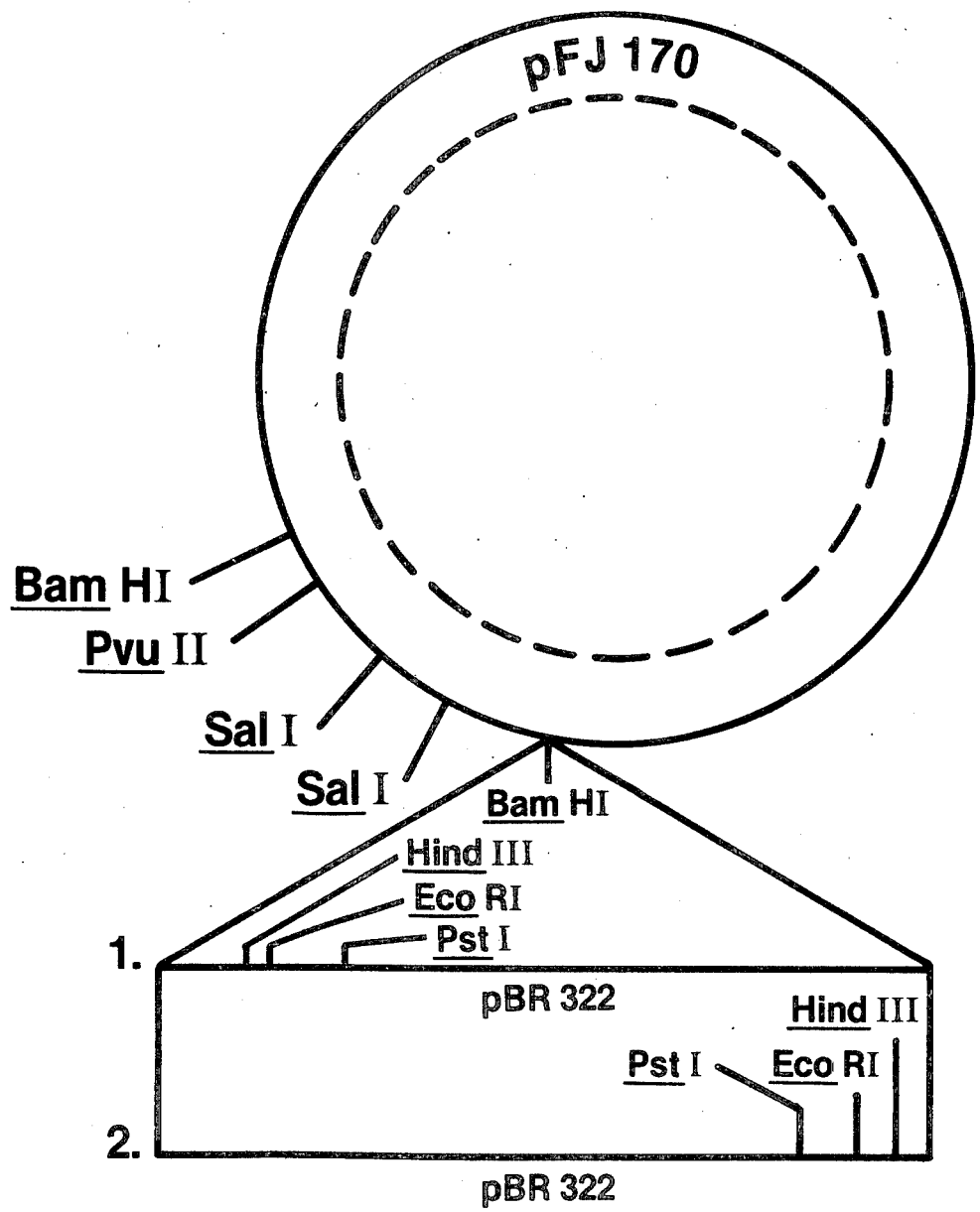

The desired chimeric plasmids are obtained by ligation of partial BamHI digest of plasmid pFJ170 (prepared according to the teaching of Example 19), and BamHI digested plasmid pBR322 (prepared in Example 6B), in substantial accordance with the ligation procedure of Example 2. The desired chimeric plasmid DNA is collected by centrifugation, washed with 70% ethanol, dried in vacuo, and then suspended in 50 μl. of TE buffer. Recombinant plasmids of two orientations result because the restricted plasmid pBR322 can be oriented in either direction. A restriction site and functional map of each of plasmids pFJ219 and pFJ220 is presented in FIG. 7 of the accompanying drawings.

EXAMPLE 24

Construction of *E. coli* K12 HB101/pFJ219 and *E. coli* K12 HB101/pFJ220

The desired constructions are made in substantial accordance with the teaching of Example 3 except that plasmid DNA from Example 23, rather than plasmid pLR2, is used for the transformation. Surviving colonies are first selected, tested for the expected phenotype (Amp$^R$, Tet$^S$) and then conventionally identified as the desired *E. coli* K12 HB101/pFJ219 and *E. coli* K12 HB101/pFJ220 transformants by restriction enzyme and agarose gel electrophoretic analysis of the constitutive plasmids (Davis, R. W. et al., 1980).

EXAMPLE 25

Construction of *Streptomyces ambofaciens*/pFJ219 and *S. ambofaciens*/pFJ220

The desired constructions are made in substantial accordance with the teaching of Example 9 except that plasmids pFJ219 and pFJ220, rather than plasmids pFJ204 and pFJ205, are used for the transformation. The resulting transformants are selected for thiostrepton resistance by the method described in Example 9 above. The thus constructed thiostrepton resistant *Streptomyces ambofaciens*/pFJ119 and *S. ambofaciens*/pFJ220 colonies are isolated according to known procedures and then conventionally identified by restriction enzyme and agarose gel electrophoretic analysis of the constitutive plasmids.

Representative plasmids and transformants constructed in accordance with the foregoing teaching include the following listed in Tables 1 and 2 below.

TABLE 1
Representative Plasmids

| Example No. | Plasmid Name | Size in kb | Construction |
|---|---|---|---|
| 26 | pFJ221 | 8.8 | Ligation of partial BamHI digest of pFJ205 and ~3.4 kb BamHI fragment of pLR1. Insertion site and orientation such that the PvuII site and the terminal SalI site of the thiostrepton and neomycin resistance fragments are adjacent. |
| 27 | pFJ222 | 8.8 | Reverse orientation of pFJ221. |
| 28 | pFJ223 | 9.0 | Ligation of partial BamHI digest of pFJ210 and ~3.4 kb BamHI fragment of pLR1. Insertion site and orientation such that the PvuII site and the terminal SalI site of the thiostrepton and neomycin resistance fragments are adjacent. |
| 29 | pFJ224 | 9.0 | Reverse orientation of pFJ223. |
| 30 | pFJ225 | 10.7 | Ligation of partial BamHI digest of pNM100 and ~1.6 kb BamHI fragment of pLR2. Orientation of ~1.6 kb fragment is the same as in pFJ204 and insertion is at site A as shown in FIG. 1. |
| 31 | pFJ226 | 10.7 | Reverse orientation of pFJ225. |
| 32 | pFJ227 | 12.5 | Ligation of partial BamHI digest of pNM100 and ~3.4 kb BamHI fragment of pLR1. Orientation of ~3.4 kb fragment is the same as in pFJ206 and insertion is at site A as shown in FIG. 1. |
| 33 | pFJ228 | 12.5 | Reverse orientation of pFJ227. |
| 34 | pFJ229 | 14.1 | Ligation of partial BamHI digest of pFJ225 and ~3.4 kb BamHI fragment of pLR1. Insertion site and orientation such that the PvuII site and the terminal SalI site of the thiostrepton and neomycin resistance fragments are adjacent. |
| 35 | pFJ230 | 14.1 | Reverse orientation of pFJ229. |
| 36 | pFJ231 | 14.1 | Ligation of partial BamHI digest of pFJ226 and ~3.4 kb BamHI fragment of pLR4. Insertion site and orientation such that the PvuII site and the terminal PstI site of the thiostrepton and neomycin resistance fragments are adjacent. |
| 37 | pFJ232 | 14.1 | Reverse orientation of pFJ231. |
| 38 | pFJ233 | 11.9 | Ligation of partial BamHI digest of pNM100 and ~2.8 kb SalI fragment (provided with BamHI linkers) of pIJ43. Orientation of ~2.8 kb fragment is the same as in pFJ215 and insertion is at the A site as shown in FIG. 1. |
| 39 | pFJ234 | 11.9 | Reverse orientation of pFJ233. |
| 40 | pFJ235 | 11.5 | Ligation of partial BamHI digest of pFJ208 and ~2.7 kb SalI-BglII fragment (provided with BamHI linkers) of pIJ43. Insertion site and orientation such that the terminal PstI sites of the neomycin and erythromycin resistance fragments are adjacent. |
| 41 | pFJ236 | 11.5 | Reverse orientation of pFJ235. |
| 42 | pFJ237 | 7.0 | Ligation of ~4 kb BamHI fragment (provided with HindIII linkers) of pFJ143 and ~3 kb HindIII fragment of pIJ43. Insertion site and orientation of resistance fragment are the same as in pFJ215. |
| 43 | pFJ238 | 7.0 | Reverse orientation of pFJ237. |
| 44 | pFJ239 | 9.7 | Ligation of partial BamHI digest of pFJ204 and ~4.3 kb BamHI fragment of pBR322. Insertion site and orientation of resistance fragment are the same as in pFJ219. |
| 45 | pFJ240 | 9.7 | Reverse orientation of pFJ239. |
| 46 | pFJ241 | 10.2 | Ligation of partial BamHI digest of pFJ205 and ~4.8 kb BamHI fragment of pBR328. Insertion site and orientation of resistance fragment are the same as in pFJ219. |
| 47 | pFJ242 | 10.2 | Reverse orientation of pFJ241. |
| 48 | pFJ243 | 12.0 | Ligation of partial BamHI digest of pFJ206 and ~4.8 kb BamHI fragment of pBR328. Insertion site of pBR328 is adjacent to the terminal PstI site of the neomycin resistance fragment and the orientation is the same as in pFJ219. |
| 49 | pFJ244 | 12.0 | Reverse orientation of pFJ243. |
| 50 | pFJ245 | 11.5 | Ligation of partial BamHI digest of pFJ207 and ~4.3 kb BamHI fragment of pBR322. Insertion site of pBR322 is adjacent to the terminal SalI site of the neomycin resis- |

TABLE 1-continued

Representative Plasmids

| Example No. | Plasmid Name | Size in kb | Construction |
|---|---|---|---|
| | | | tance fragment and the orientation is the same as in pFJ219. |
| 51 | pFJ246 | 11.5 | Reverse orientation of pFJ245. |
| 52 | pFJ247 | 13.6 | Ligation of partial BamHI digest of pFJ208 and ~4.8 kb BamHI fragment of pBR328. Insertion site of pBR328 is adjacent to the terminal PstI site of the neomycin resistance fragment and the orientation is the same as in pFJ219. |
| 53 | pFJ248 | 13.6 | Reverse orientation of pFJ247. |
| 54 | pFJ249 | 10.4 | Ligation of partial BamHI digest of pFJ170 and ~4.8 kb BamHI fragment of pBR328. Insertion site and orientation of resistance fragment are the same as in pFJ219. |
| 55 | pFJ250 | 9.9 | Reverse orientation of pFJ249. |
| 56 | pFJ251 | 11.8 | Ligation of partial BamHI digest of pFJ237 and ~4.8 kb HindIII fragment of pBR328. Insertion is at the HindIII site that is adjacent to the SmaI site of pFJ143. Orientation is the same as in pFJ219. |
| 57 | pFJ252 | 11.8 | Reverse orientation of pFJ251. |
| 58 | pFJ253 | 17.3 | Ligation of partial BamHI digest of pFJ233 and ~5.4 kb BamHI fragment of pBR325. Insertion site of pBR325 is at the A site as shown in FIG.1 and the orientation is the same as in pFJ219. |
| 59 | pNM101 | 10.1 | Ligation of partial BamHI digest of pNM100 and the ~.8 kb BclI subfragment of the ~1.6 kb BamHI fragment of pLR2. Orientation of BclI fragment is the same as in pFJ204 and insertion is at site A as shown FIG. 1. |
| 60 | pNM102 | 10.1 | Reverse orientation of pNM101. |
| 61 | pNM103 | 4.6 | Ligation of the ~3.8 kb BamHI fragment of pNM101 and the ~.8 kb BclI subfragment of the ~1.6 kb BamHI fragment of PLR2. Orientation of BclI fragment is the same as in pNM101. |
| 62 | pNM104 | 4.6 | Reverse orientation of pNM103. |
| 63 | pFJ265 | 9.2 | Ligation of partial PstI digest of pLR4 with PstI digested plasmid pNM103. Orientation such that the EcoRI site of the pLR4 fragment is opposite (not adjacent and closest to) the thiostrepton resistance-conferring segment of pNM103. |
| 64 | pFJ266 | 9.2 | Reverse orientation of pFJ265. |

TABLE 2

Representative Transformants

1. *Streptomyces* R/R$^1$ wherein R is *ambofaciens, aureofaciens, griesofuscus, fradiae, lividans, granuloruber, tenebrarius,* or *cinnamonensis* and wherein R$^1$ independently is plasmid pFJ204, pFJ205, pFJ206, pFJ207, pFJ208, pFJ209, pFJ143, pFJ170, pFJ210, pFJ211, pFJ212, pFJ213, pFJ214, pFJ215, pFJ216, pFJ219, pFJ220, or any plasmid listed in Table 1.
2. *E. coli* R$^2$/R$^3$ wherein R$^2$ is K12 or K12 HB101 and wherein R$^3$ independently is plasmid pFJ239, pFJ240, pFJ241, pFJ242, pFJ243, pFJ244, pFJ245, pFJ246, pFJ247, pFJ248, pFJ249, pFJ250, pFJ251, pFJ252, or pFJ253.

I claim:

1. A recombinant DNA cloning vector comprising:
   (a) a functional origin of replication-containing restriction fragment of plasmid pNM100 and
   (b) one or more DNA segments that confer resistance to at least one antibiotic when transformed into a sensitive host cell, said host cell being susceptible to transformation, cell division, and culture.

2. The cloning vector of claim 1 wherein the restriction fragment of pNM100 is the ~3.8 kb BamHI restriction fragment.

3. The cloning vector of claim 1 wherein the restriction fragment of pNM100 is the ~4 kb BamHI restriction fragment of plasmid pFJ143.

4. The cloning vector of claim 1 wherein one DNA segment confers antibiotic resistance to thiostrepton.

5. The cloning vector of claim 1 wherein one DNA segment confers antibiotic resistance to neomycin.

6. The cloning vector of claim 1 wherein one DNA segment confers antibiotic resistance to erythromycin.

7. The cloning vector of claim 1 wherein one DNA segment is the ~1.6 kb BamHI restriction fragment of plasmid pLR2.

8. The cloning vector of claim 1 wherein one DNA segment is the ~3.4 kb BamHI restriction fragment of plasmid pLR1.

9. The cloning vector of claim 1 wherein one DNA segment is selected from the group consisting of the ~2.8 kb SalI, ~2.7 kb SalI-BglII, ~3.0 kb HindIII, ~2.5 kb SalI-BamHI, ~2.8 kb XhoI-BglII, and the ~4.1 kb EcoRI-BamHI restriction fragments of plasmid pIJ43.

10. The recombinant DNA cloning vector of claim 1 which is selected from the group consisting of plasmids pFJ204, pFJ205, pFJ206, pFJ207, pFJ208, pFJ209, pFJ170, pFJ210, pFJ211, pFJ212, pFJ213, pFJ214, pFJ215, pFJ216, pFJ221, pFJ222, pFJ223, pFJ224, pFJ225, pFJ226, pFJ227, pFJ228, pFJ229, pFJ230, pFJ231, pFJ232, pFJ233, pFJ234, pFJ235, pFJ236, pFJ237, pFJ238, pNM101, pNM102, pNM103, pNM104 pFJ265 and pFJ266.

11. The recombinant DNA cloning vector of claim 10 which is pFJ204.

12. The recombinant DNA cloning vector of claim 10 which is pFJ205.

13. The recombinant DNA cloning vector of claim 10 which is pFJ206.

14. The recombinant DNA cloning vector of claim 10 which is pFJ207.

15. The recombinant DNA cloning vector of claim 10 which is pFJ208.

16. The recombinant DNA cloning vector of claim 10 which is pFJ209.

17. The recombinant DNA cloning vector of claim 10 which is pFJ170.

18. The recombinant DNA cloning vector of claim 10 which is pFJ210.

19. The recombinant DNA cloning vector of claim 10 which is pNM101.

20. The recombinant DNA cloning vector of claim 10 which is pFJ212.

21. The recombinant DNA cloning vector of claim 10 which is pFJ213.

22. The recombinant DNA cloning vector of claim 10 which is pNM103.

23. The recombinant DNA cloning vector of claim 10 which is pFJ215.

24. The recombinant DNA cloning vector of claim 10 which is pFJ216.

25. The recombinant DNA cloning vector of claim 10 which is pFJ222.

26. The recombinant DNA cloning vector of claim 10 which is pFJ224.

27. The recombinant DNA cloning vector of claim 10 which is pFJ233.

28. The recombinant DNA cloning vector of claim 10 which is pFJ235.

29. A recombinant DNA cloning vector which comprises a replicon that is functional in *E. coli,* a DNA segment that confers antibiotic resistance in *E. coli* and a restriction fragment comprising a recombinant DNA cloning vector of claim 1.

30. The recombinant DNA cloning vector of claim 29 in which the replicon that is functional in *E. coli* and the DNA segment that confers antibiotic resistance in *E. coli* comprise a restriction fragment of a plasmid selected from the group consisting of plasmids pBR322, pBR324, pBR325, and pBR328.

31. The recombinant DNA cloning vector of claim 30 which is pFJ219.

32. The recombinant DNA cloning vector of claim 30 which is pFJ239.

33. The recombinant DNA cloning vector of claim 30 which is pFJ247.

34. The recombinant DNA cloning vector of claim 30 which is pFJ253.

35. A transformed restrictionless *Streptomyces* host cell comprising a recombinant DNA cloning vector of claim 1.

36. A transformed restrictionless *Streptomyces* host cell comprising a recombinant DNA cloning vector of claim 10.

37. The transformed host cell of claim 36 which is selected from the group consisting of *Streptomyces ambofaciens, Streptomyces aureofaciens, Streptomyces griseofuscus, Streptomyces fradiae, Streptomyces lividans, Streptomyces granuloruber, Streptomyces tenebrarius,* and *Streptomyces cinnamonensis.*

38. The transformed host cell of claim 37 which is *Streptomyces ambofaciens*/pFJ204.

39. The transformed host cell of claim 37 which is *Streptomyces griseofuscus*/pFJ205.

40. The transformed host cell of claim 37 which is *Streptomyces aureofaciens*/pFJ206.

41. The transformed host cell of claim 37 which is *Streptomyces fradiae*/pFJ207.

42. The transformed host cell of claim 37 which is *Streptomyces ambofaciens*/pFJ208.

43. The transformed host cell of claim 37 which is *Streptomyces ambofaciens*/pFJ170.

44. A transformed *E. Coli* host cell comprising a recombinant DNA cloning vector of claim 29.

45. A transformed *E. Coli* host cell comprising a recombinant DNA cloning vector of claim 30.

46. A transformed host cell comprising the recombinant DNA cloning vector of claim 29 which is restrictionless *Streptomyces E. coli.*

47. The transformed host cell of claim 45 which is *E. coli* K12 HB101/pFJ219.

48. The transformed host cell of claim 45 which is *E. coli* K12 HB101/pFJ239.

49. The transformed host cell of claim 45 which is *E. coli* K12 HB101/pFJ253.

50. Plasmid pNM100 isolated from *Streptomyces virginiae*/pNM100 of claim 1.

51. The ~3.8 kb BamHI restriction fragment of claim 2.

52. The ~4 kb BamHI restriction fragment of claim 3.

53. Plasmid pFJ143 of claim 3.

54. The recombinant DNA cloning vector of claim 10 which is pFJ265.

55. The recombinant DNA cloning vector of claim 10 which is pFJ266.

56. The transformed host cell of claim 37 which is *Streptomyces ambofaciens*/pFJ265.

57. The transformed host cell of claim 37 which is *Streptomyces ambofaciens*/pFJ266.

* * * * *

UNITED STATES PATENT AND TRADEMARK OFFICE
CERTIFICATE OF CORRECTION

PATENT NO. : 4,468,462

DATED : August 28, 1984

INVENTOR(S) : Nancy E. Malin, Jeffrey T. Fayerman, Michael D. Jones, James A. Mabe, Walter M. Nakatsukasa It is certified that error appears in the above-identified patent and that said Letters Patent are hereby corrected as shown below:

In column 2, line 26, insert -- containing -- between "replication" and "restriction".

In column 10, line 45, insert -- reaction -- between "µl." and "mix" on line 46.

In column 10, line 46, insert -- BSA-- between "µl." and (1 mg./ml.)".

In column 19, in the heading of Table I, insert -- ~ -- before "Size" in the third column.

In column 21, in the heading of Table I. insert -- ~ -- before "Size" in the third column.

In column 24, Claim 46, "Streptomyces E. Coli" should be changed to -- Streptomyces --.

Signed and Sealed this

Twenty-sixth Day of March 1985

[SEAL]

Attest:

DONALD J. QUIGG

Attesting Officer

Acting Commissioner of Patents and Trademarks